United States Patent [19]

Hostetter et al.

[11] Patent Number: 4,911,913
[45] Date of Patent: Mar. 27, 1990

[54] MULTIPLE EMBEDDED NUCLEAR POLYHEDROSIS VIRUS FROM CELERY LOOPER WITH ACTIVITY AGAINST LEPIDOPTERA

[75] Inventors: Donald L. Hostetter, Twin Falls, Id.; Benjamin Puttler, Columbia, Mo.

[73] Assignee: The United States of America as represented by the Secretary of Agriculture, Washington, D.C.

[21] Appl. No.: 320,126

[22] Filed: Mar. 7, 1989

[51] Int. Cl.$^4$ .................. A01N 63/02; C12N 7/00
[52] U.S. Cl. ...................................... 424/93; 435/235
[58] Field of Search ..................... 435/235; 424/93

[56] References Cited

U.S. PATENT DOCUMENTS 4,186,195  1/1980  Yearian ............................ 424/93
4,789,632  12/1988  Groner ............................ 435/235
4,844,896  7/1989  Bohm et al. ..................... 424/93

Primary Examiner—Sam Rosen
Attorney, Agent, or Firm—M. H. Silverstein; Mervin E. Brokke; J. D. Fado

[57] ABSTRACT

A multiple embedded nuclear polyhedrosis virus isolated from the celery looper, *Syngrapha falcifera*, was found to have broad insecticidal activity against *lepidoptera* species.

5 Claims, No Drawings

MULTIPLE EMBEDDED NUCLEAR POLYHEDROSIS VIRUS FROM CELERY LOOPER WITH ACTIVITY AGAINST LEPIDOPTERA

BACKGROUND OF THE INVENTION

1. Field of the Invention

This invention relates to a multiple embedded nuclear polyhedrosis virus isolated from a celery lopper, Syngrapha falcifera, with broad host spectrum activity in Lepidoptera.

2. Abbreviations

Abbreviations or definitions used in the disclosure are as follows: AcMEV, *Autographa california* Multiple Embedded; HPV-85-CLMEV, Celery Looper Multiple Embedded; DOC, Sodium Deoxychlolate; HaMEV, *Heliothis armigera* Multiple Embedded; IB, Inclusion Bodies; MEIB, Multiple Embedded Inclusion Bodies; MENPV, Multiple Embedded Nuclear Polyhedrosis Virus; MEV, Multiple Embedded; NPV, Nuclear Polyhedrosis Virus; OS, Original Suspension; PIB, Polyhedra Inclusion Body(ies); REN, Restriction Endonuclease; SDW, Sterile Distilled Water; SEV, Single Embedded; SoMEV, *Spodoptera ornithogalli* Multiple Embedded; TEM, Transmission Electron Microscopy.

3. Summary of the Prior Art

A number of laboratories have investigated the control of insects by microbial agents, including viruses, bacteria, fungi, and protozoa. It is expected that microbial insecticides will be toxic to specific pests and not to other life forms in the environment. Microbial insecticides are thought to be rapidly inactivated when exposed to the environment and to degrade quickly to nontoxic molecules [see A. Senuta, Agrichemical Age, p. 21 (January 1987)].

Although there are potential advantages to viral insecticides, the use of these materials has been inhibited by high costs of developing and marketing, the need for precise timing of application, and great specificity to a limited number of insect species.

Four virus insecticides have been registered for use in the United States [Senuta, supra; Betz, Registration of Baculoviruses as Pesticides. In "The Biology of Baculoviruses, Vol. II. Practical Application for Insect Control," R. R. Granados and B. A. Federici, eds., CRC Press Inc., Boca Raton, FL, 320 pp. (1986)]. These include polyhedrosis Heliothis commercially known as "Viron H" and most recently as "ELCAR" for cotton bollworm and tobacco budworm, tussock moth larvae, gypsy moth larvae, and pine sawfly larvae.

Polyhedrosis viruses have been isolated from *Heliothis zea* [Ignoffo, J. Invertebr. Pathol. 7: 315–319 (1965)], *Autographa californica* [Vail et al., J. Invertebr. Pathol. 17: 383–388 (1971)], and *Heliothis armigera* [Williams and Payne, Ann. Appl. Biol. 104: 405–412 (1984)]. [See Chauthani and Rehnborg, J. Invertebr. Pathol. 17: 234–237 (1971), and Shapiro, In vivo Production of Baculoviruses, In "The Biology of Baculoviruses, Vol. II. Practical Application for Insect Control," R. R. Granados and B. A. Federici, eds., CRC Press Inc., Boca Raton, FL (1986)]. There is no known reported isolation of virus from the celery looper, *Syngrapha falcifera*.

The virus of the present invention was compared with other closely known related viruses described above by restriction endonuclease analysis (REN) and with AcMEV, which is known to have a wide host range. The REN patterns clearly show that the virus of the present invention is distinct from the known viruses.

SUMMARY OF THE INVENTION

It is an object of this invention to disclose a new virus isolated from the celery looper, *Syngrapha falcifera*, which is useful for the control of insect pests.

Another object of the invention to to teach a method of controlling insect pests by the application of the new baculovirus to insect habitats.

Additional objects of the invention will be set forth in the description which follows, and will become apparent to those skilled in the art upon examination of the specification or by practice of the invention.

DETAILED DESCRIPTION OF THE INVENTION

The virus described in this invention is designated Celery Looper Multiple Embedded Virus (HPV-85-CLMEV). It is continuously maintained by the United States Department of Agriculture, Soil and Water Research, Route 1, Box 186, Kimberly, Idaho 83341. The virus has been accepted for deposit under the conditions of the Budapest Treaty with the American Type Culture Collection, 12301 Parklawn Drive, Rockville, MD 2052, and assigned ATCC Accession No. VR 2237..

Several 4th instar looper larvae collected from cabbage plants at Prairie Home, Copper County, Mo., were held in the laboratory on artificial diet for observation and possible parasite emergence. After two days, two of the larvae exhibited signs typical of nucleopolyhedrosis in lepidoptera and died [Aizawa, In "Insect Pathology. An advanced Treatise," E. A. Steinhaus, ed., Vol. 1, pp. 381–412, Academic Press, New York & London (1963)]. These larvae were isolated and examined microscopically; numerous inclusion bodies (IB) with various sizes and morphological characteristics were observed in the examined tissue. The cadavers were then triturated in 3.0 ml of sterile distilled water (SDW); the homogenate was filtered through nylon organdy, and aliquots were prepared for bioassay and transmission electron microscopy (TEM). Noninfected larvae from the same sample were reared to ecolsion and determined to be celery loopers, *Syngrapha falcifera* (Kirby).

The number of IB/ml of original suspension (OS) was determined to be $1.4 \times 10^8$. An aliquot of the OS was serially diluted and bioassayed against neonate celery looper and 24-hr-old cabbage looper, *Trichoplusia ni* (Hübner) larvae [Ignoffo and Boening, J. Econ. Entomol. 63: 1696–1697 (1970)]. All larvae were dead and liquefied within 10 days post treatment. Microscopic examination (500X phase contrast) of infected tissues revealed numerous TB ranging in size from 1.6 to 2.6 $\mu$m, with large EIB predominating (ca. ratio 3:1). Morphological differences observed between IB suggested that Single Embedded (SEV) and Multiple Embedded (MEV) were present. Subsequent transmission electron microscopy of sectioned IB from the original isolate did confirm the presence of SEV; however, extensive searching of the examined grids indicated that the Multiple Embedded Inclusion Bodies (MEIB) were the predominant form.

*T. ni* larvae were found to be suitable for propagtion of HPV-85-CLMEV. Serial dilutions (200, 100, 50, 15, 10, and 1.0 IB/mm$^2$) of a suspension containing 1,000 IB/0.1 ml (stored frozen) were made to ensure eliminating bacterial contaminants through dilution. Those larvae (25 in each of the 6 treatments) dying at the lowest concentration of IB were selected and used for further propagation. All treated *T. ni* larvae were dead and liquefying within four days; 12 larvae from the two lowest concentrations were examined and found to be free of bacterial contaminants. Two of these larvae contained only the large IB; they were triturated in SDW, and the IB's were separated, washed, and concentrated via differential centrifugation. This suspension was free of bacteria and was the source of all other propagation and testing.

Pathology, Microscopy, and Restriction Endonuclease

Larvae infected with the HPV-85-CLMEV exhibited visual signs typical of nucleopolyhedrosis in lepidopteran larvae [Aizawa, supra]. They became lethargic, ceased feeding, and turned milky-white prior to death, followed by general melanization and rupture of the integument (liquefaction). IB were observed in the nuclei of cells from fat body, tracheal matrix, hemocytes, and epidermis. The mean diameter of randomly selected IB was $1.87 \pm 0.09$ μm SD (range=2.0 to 3.0 μm, n=10) based on ocular micrometer measurements (500X phase contrast). Electron micrographs indicated that nucleocapsids (virions) were multiple-embedded with numerous bundles per IB.

The unique fragmentation pattern of HPV-85-CLMEV DNA produced by restrictive endonuclease analysis is conclusive evidence that it is different from other related viruses.

Prepagation of Stock Suspensions and Bioassays

HPV-85-CLMEV and AcMEV were easily propagated in T. ni larvae; the harvesting protocol was rapid, and the IB's were readily separated by centrifugation. Bacterial contamination was a minor incovenience on occasion and was traced to the artificial diet. The virus suspensions used as inocula were free of bacterial. Several attempts were made to physically eliminate contaminants via selection of uniformly appearing infected larvae. Collecting dead larvae and freezing them prior to liquefaction was the most effective method. Larvae were also removed from the artificial diet and placed in sterile petri dishes prior to death. They were then incubated at 30° C. until death and allowed to liquefy. The homogenate was then combined with SDW and the IB collected by centrifugation. The AcMEV preparation was treated with a 3.3% solution of sodium deoxycholate (DOC) to lyse bacteria and other cells. This procedure was very effective and resulted in a virtually pure suspension of IB. This technique is routinely used to prepare pure IB suspensions prior to the alkali release of the nucleocapsids and REN characterization.

Dose-Mortality, Time-Mortality, and Susceptibility Tests

Routine bioassays, comparisons between HPV-85-CLMEV and AcMEV, and susceptibility tests were all conducted with aliquots of each of the OS. Activity of the AcMEV against *T. ni* ($LC_{50}=0.32$ IB/mm$^2$) was identical to that reported by Vail et al. [Environ. Entomol. 11: 1187–1192 (1982)]. All bioassay data represent at least four replicates of 50 larvae each, and all comparative bioassays were conducted concomitantly. Routine susceptibility tests were not always replicated. However, all larvae reported as being susceptible were examined microscopically and a photographic record was made of representative, infected tissue. In the case of the *Manduca sexta* larva, IB was collected from infected larvae (*M. sexta*) and bioassayed against neonate *T. ni*; all *T. ni* larvae died and liquefied within three days, and HPV-85-CLMEV IB were present. The susceptibility tests were also administered at a concentration of 100 IB/mm$^2$, which was comparable to application rates recommended for the commercially registered viral insecticide "ELCAR" (4 oz/acre, A.I. $4 \times 10^9$ PIB/g). This provided a realistic and relatively conservative estimate of susceptibility.

The results of bioassays indicated that the HPV-85-CLMEV was very active against *Syngrapha falcifera, Trichoplusia ni, Heliothis zea*, and *H. virescens* larvae and was able to infect 33 species from 10 families in the order Lepidoptera (Table V).

Table I summarizes the results of dose-mortality responses of *S. falcifera* and *T. ni* neonatal larvae to similar concentrations of HPV-85-CLMEV and AcMEV. *T. ni* larvae are more susceptible to HPV-85-CLMEV at all concentrations than were the *S. falcifera* larvae.

The HPV-85-CLMEV is a broad spectrum, very active, multiple embedded, nuclear polyhedrosis virus. Comparison with published data indicate that this isolate is much more active against Heliothis complex than the previously developed product "ELCAR" (Heliothis single embedded virus) [Ignoffo, J. Invertebr. Pathol. 7: 315–319 (1965); Ignoffo, J. Invertebr. Pathol. 8: 531–536 (1966); Ignoffo and Couch, In Microbial Control of Pests and Plant Diseases 1970-1980, H. D. Burges (ed.), pp. 330-362, Academic Press Inc., London (1981)].

The rapidity of larvae mortality and the differences in $LT_{50}$ values for HPV-85-CLMEV and AcMEV are shown in Table II.

TABLE I

Dose-Mortality Response of Neonate *Syngrapha falcifera* and *Trichoplusia ni* to HPV-85-CLMEV

| Dose IB/mm$^2$ | Syngrapha falcifera Replication - % Mortality, 10 days | | | | | Trichoplusia ni Replication - % Mortality, 10 days | | | | |
|---|---|---|---|---|---|---|---|---|---|---|
| | 1 | 2 | 3 | 4 | X ± SEM | 1 | 2 | 3 | 4 | X ± SEM |
| 0.75 | 93.33 | 100 | 85.71 | 79.59 | 89.66 ± 6.36 | 87.76 | 94.12 | 100 | 90.20 | 93.02 ± 9.77 |
| 0.50 | 75.00 | 87.50 | 60.00 | 76.09 | 74.65 ± 5.27 | 62.50 | 78.00 | 95.92 | 81.63 | 79.51 ± 9.08 |
| 0.25 | 56.25 | 82.00 | 63.04 | 58.33 | 64.91 ± 7.17 | 66.00 | 80.00 | 82.35 | 54.90 | 70.81 ± 8.38 |
| 0.10 | 35.56 | 52.08 | 34.69 | 25.00 | 36.83 ± 8.78 | 31.37 | 32.69 | 42.86 | 35.29 | 35.55 ± 4.58 |
| 0.05 | 27.66 | 30.00 | 25.00 | 13.04 | 23.93 ± 4.99 | 16.33 | 20.00 | 34.00 | 25.00 | 23.83 ± 5.17 |

TABLE II

LT$_{50}$ for HPV-85-E CLMEV and AcMEV at Concentrations of 10 and 100 IB/mm$^2$ Against Neonate Larvae of Five Species of Lepidoptera

| | LT$_{50}$ - Days | | | |
|---|---|---|---|---|
| | HPV-85-CLMEV | | AcMEV | |
| Species | 10 IB/mm$^2$ | 100 IB/mm$^2$ | 10 IB/mm$^2$ | 100 IB/mm$^2$ |
| *Heliothis zea* | 4.4 | 4.2 | 7.8 | 7.4 |
| *H. virescens* | 2.8 | 2.6 | 3.5 | 3.0 |
| *H. subflexa* | 3.3 | 2.6 | 3.5 | 3.0 |
| *Agrotis ipsilon* | 4.7 | 4.7 | 0 | 6.6 |
| *Spodoptera frugiperda* | 3.3 | 2.6 | 0 | 2.9 |

The susceptibility and rapid kill of *A. ipsilon* larvae is of particular interest in the comparison of HPV-85-CLMEV and AcMEV. Table III shows the response of 10 species to 3 concentrations of HPV-85-CLMEV and AcMEV. The HPV-85-CLMEV is active against all 10 species, with 100% mortality occurring in 7 of the 10 species tested within 10 days. The AcMEV caused 100% mortality in 3 of the 10 species tested and did not infect (i.e., no mortality occurred amongst larvae challenged with HPV-85-CLMEV) *Piersis rapae, Peridroma saucia*, or *Diacrisia virginica*. The HPV-85-CLMEV is clearly more active at these concentrations than the AcMEV. The differences in activity between HPV-85-CLMEV and AcMEV are evident in the LC$_{50}$ values generated through bioassays (Table IV). When LC$_{50}$ values of HPV-85-CLMEV and AcMEV against *H. zea* larvae are compared, the HPV-85-CLMEV demonstrates a 28.6% increase in bioassay activity over the AcMEV.

Table V presents a summary of species challenged with HPV-85-CLMEV at a concentration of 100 to 200 IB/mm$^2$ of diet substrate. This list, although not all inclusive, demonstrates the wide spectrum of the HPV-85-CLMEV. The ability of the HPV-85-CLMEV to successfully infect the black cutworm, fall webworm, velvet bean caterpillar, tobacco budworm, corn earworm, cabbage looper, soybean looper, fall armyworm, codling moth, imported cabbage worm, navel orangeworm, diamond backed moth, European corn borer, sunflower moth, almond moth, Mediterranean flour moth, and raisin moth, in addition to 16 other lepidopterans, will be of particular value in developing broad spectrum approaches to reducing insect populations. No other MENPV has been reported to successfully infect such a large portion of economiclly important species of insects.

As a practical matter, it is envisioned that commercial formulations of the subject viral pesticidal agent would be prepared directly from culture media such as larval homogenates, or fractions derived from such homogenates, thereby obviating the need to isolate the virus in pure form. Other suitable means could be readily determined by the skilled artisan.

TABLE III

A Comparison of HPV-85-CLMEV and AcMEV at Three Concentrations Against Neonate Larvae of Various Lepidopterous Hosts[a]

| | % Mortality | | | | | | | | | | | |
|---|---|---|---|---|---|---|---|---|---|---|---|---|
| | HPV-85-CLMEV | | | | | | AcMEV | | | | | |
| | 5 days | | | 10 days | | | 5 days | | | 10 days | | |
| IB/mm$^2$ | 100 | 10 | 1.0 | 100 | 10 | 1.0 | 100 | 10 | 1.0 | 100 | 10 | 1.0 |
| *Heliothis zea* | 80 | 96 | 0 | 100 | 100 | 19 | 18 | 16 | 0 | 56 | 52 | 0 |
| *H. virescens* | 100 | 100 | 0 | — | — | 79 | 100 | 100 | 0 | — | — | 0 |
| *H. subflexa* | 100 | 100 | 0 | — | — | 67 | 100 | 100 | 0 | — | — | 0 |
| *Spodoptera frugiperda* | 98 | 74 | 0 | 100 | 74 | 4 | 70 | 21 | 0 | 74 | 21 | 0 |
| *S. ornithogalli* | 100 | 96 | 0 | 100 | 100 | 5 | 98 | 89 | 0 | 100 | 95 | 0 |
| *Agrotis ipsilon* | 57 | 64 | 0 | 71 | 88 | 3 | 43 | 28 | 0 | 59 | 36 | 0 |
| *Anticarsia gemmatalis* | 52 | 8 | 0 | 100 | 81 | 6 | 4 | 0 | 0 | 94 | 30 | 0 |
| *Pieris rapae* | 7 | 0 | 0 | 13 | 0 | 0 | 0 | 0 | 0 | 0 | 0 | 0 |
| *Peridroma saucia* | 24 | 0 | — | 44 | 6 | — | 0 | 0 | 0 | 0 | 0 | 0 |
| *Diacrisia virginica*[b] | 100 | 0 | — | 100 | 0 | — | 0 | 0 | 0 | 0 | 0 | 0 |

[a]ca. 50 larvae/concentration
[b]2 to 3d instar larvae

TABLE IV

Extrapolated LC$_{50}$ Values of HPV-85-CLMEV and AcMEV Assayed Against Neonate Larvae[a]

| Species | HPV-85-CLMEV IB/mm$^2$ | AcMEV IB/mm$^2$ | Rel. Sus. |
|---|---|---|---|
| *Heliothis zea* | 0.36 | 10.3 | 28.6x |
| *H. virescens* | 0.35 | 0.45 | 1.3x |
| *Trichoplusia ni* | 0.15 | 0.32 | 2.1x |
| *Syngrapha falcifera* | 0.15 | —[b] | — |

[a]4 replicates, 50 larvae/replicate
[b]AcMEV not assayed against *S. falcifera* larvae

TABLE V

Susceptibility of Various Insect Species[a] Challenged Per Os to HPV-85-CLMEV[b] on Artificial or Natural Host-Plant Material

SUSCEPTIBLE

I. LEPIDOPTERA

A. Arctiidae

| | |
|---|---|
| 1. *Diacrisia virginica* (F.) | yellow woolly bear |
| 2. *Hyphantria cunea* (Drury) | fall webworm |

B. Geometridae

| | |
|---|---|
| 1. *Paleacrita vernata* (Peck) | spring cankerworm[c] |

C. Hesperiidae

| | |
|---|---|
| 1. *Staphylus hayhurstii* (Edwards) | southern sootywing[d] |

D. Noctuidae

| | |
|---|---|
| 1. *Agrotis ipsilon* (Hufnagel) | black cutworm[c] |
| 2. *Anticarsia gemmatalis* (Hubner) | velvetbean caterpillar |
| 3. *Autographa biloba* (Stephens) | |
| 4. *Ceramica picta* (Harris) | zebra caterpillar |
| 5. *Heliothis subflexa* (Guenee) | |
| 6. *Heliothis virescens* (F.) | Tobacco budworm |
| 7. *Heliothis zea* (Boddie) | corn earworm. |

TABLE V-continued

Susceptibility of Various Insect Species[a] Challenged Per Os to HPV-85-CLMEV[b] on Artificial or Natural Host-Plant Material

| | |
|---|---|
| 8. *Peridroma saucia* (Hubner) | cotton bollworm, tomato fruitworm variegated cutworm |
| 9. *Pseudoplusia includens* (Walker) | soybean looper |
| 10. *Spodoptera fruigiperda* (J. E. Smith) | fall armyworm |
| 11. *Spodoptera ornithogalli* (Guenée) | yellowstriped armyworm |
| 12. *Trichoplusia ni* (Hubner) | cabbage looper |
| E. Olethreutidae | |
| 1. *Laspeyresia pomonella* (L.) | codling moth[f] |
| F. Pieridae | |
| 1. *Pieris rapae* (L.) | imported cabbageworm |
| 2. *Colias eurytheme* (Boisduval) | alfalfa caterpillar |
| G. Pyralidae | |
| 1. *Amyelois transitella* (Walker) | navel orangeworm[f] |
| 2. *Anagasta kuekniella* (Zeller) | Mediterranean flour moth[f] |
| 3. *Cadra figulilella* (Evegson) | raisin moth[c] |
| 4. *Diatraea grandiosella* (Dyar) | southwestern corn borer |
| 5. *Ephestia cautella* (Walker) | almond moth[f] |
| 6. *Evergestis rimosalis* (Guenee) | cross-striped cabbageworm |
| 7. *Homoeosoma electellum* (Hulst) | sunflower moth |
| 8. *Ostrinia nubilalis* (Hubner) | European corn borer |
| 9. *Plodia interpunctella* (Hubner) | Indian meal moth |
| H. Spingidae | |
| 1. *Manducca sexta* (L.) | tobacco hornworm |
| I. Yponomeutidae | |
| 1. *Plutella xylostella* (L.) | diamondbacked moth |
| NON-SUSCEPTIBLE | |
| I. LEPIDOPTERA | |
| A. Arctiidae | |
| 1. *Euchaetias egle* (Drury) | milkweed tussock moth[g] |
| B. Noctuidae | |
| 1. *Xestia c-nigrum* (L.) | spotted cutworm[e] |
| 2. *Feltia jaculifera* (Guenee) | dingy cutworm[e] |
| 3. *Feltia subterranea* (F.) | granulate cutworm[e] |
| 4. *Lacinipolia renigera* (Stephens) | bristly cutworm[e] |
| 5. *Plathypena scabra* (F.) | green cloverworm |
| C. Notodontidae | |
| 1. *Symmerista albifrons* (Hubner) | red humped oakworm[h] |
| D. Pyralidae | |
| 1. *Elasmopalpus lignosellus* (Zeiler) | lesser cornstalk borer |
| E. Sphingidae | |
| 1. *Ceratomia catalpae* (Boisduval) | catalpa sphinx[i] |
| II. COLEOPTERA | |
| A. Chrysomelidae | |
| 1. *Zygogramma suturalis* (F.) | ragweed beetle[j] |
| III. DIPTERA | |
| A. Chironomidae | |
| 1. *Chironomus riparius* Meigen | common midge[k] |
| B. Muscidae | |
| 1. *Musca domestica* (L.) | house fly[l] |

[a] Larval stages
[b] 100 IB/mm$^2$ of diet or leaf surface
[c] 139 IB/mm$^2$ diet surface
[d] Lambs quarters (*Chenopodium album*) treated foliage
[e] 250 IB/mm$^2$ diet surface
[f] 150 IB/mm$^2$ of diet; P. V. Vail, USDA-ARS, Fresno, California
[g] Climbing milkweed (*Asclepias* sp.) treated foliage
[h] Pin oak (*Quercus palustris* Muenchh.) treated foliage
[i] Catalpa (*Catalpa bignoniodes* Walt.) treated foliage
[j] Common ragweed (*Ambrosia artemisiifolia*) treated foliage
[k] 4.475 × 10$^7$ IB/ml in 50 ml water and feeding solution in 250 ml aerated beaker - 25 larvae/treatment
[l] Fly diet Of course, for applications demanding a high degree of specificity, i.e., a high level of predictability of the intended response by both target and nontarget organisms, it would normally be preferred to prepare the formulations from pure or substantially pure virus. For example, it is possible that extraneous substances in the larval material would have an undesirable effect in regard to the intended activity.

The potency of HPV-85-CLMEV dictates that it be applied in conjunction with a suitable carrier or vehicle as known in the art. Of particular interest are those which are agronomically acceptable. Inert solids such as cellulose or sugars, wettable powders, and aqueous surfactant mixtures are illustrative of suitable chemical carriers. Depending on the substrate, target species, mode of application, and type of response desired, the concentration of virus in the final composition may vary considerably, but typically should be at least about $4.0 \times 10^9$ to $4.0 \times 10^{11}$ IB/g. Factors such as phytotoxicity toward the treated plant and tolerance of nontarget species can be used by the skilled artisan in determining the maximum level.

In the case of insect pathogens such as viruses, it is desirable to use biological carriers to distribute the pathogen. Such a biological carrier may be, for example, a species of insect which is closely related to the target species, but which is itself relatively unaffected by the pathogen. In this disclosure the word "carrier" is defined to include both chemical and biological carriers.

The level of virus is administered in an amount effective to induce infection as predetermined by routine testing. Where the ultimate response is pest mortality, an "effective amount" or "pesticidally effective amount" is defined to mean those quantities of virus which will result in a significant mortality rate of a test group as compared to an untreated group. The actual effective amount may vary with the species of pest, stage of larval development, the nature of the substrate, the type of vehicle or carrier, the period of treatment, and other related factors.

To be effective, the virus must be ingested by the insect; therefore, the virus must be applied to the locus of, or the vicinity of, the pest to be controlled. In the case of plants, the virus will typically be applied to the leaf surfaces.

The viral pesticide encompassed herein is effective in controlling a variety of insects. Without desiring to be limited thereto, pests of particular interest known to be vulnerable to treatment are agronomically important insects, especially those of the order Lepidoptera.

The following examples are intended only to further illustrate the invention and are not intended to limit the scope of the invention which is defined by the claims.

EXAMPLE 1

Preparation of HPV-85-CLMEV Stock Suspension for Bioassays

The original HPV-85-CLMEV inoculum (used for propagating virus for REN) was used to produce a stock suspension for future bioassays. *T. ni* larvae (mid-4th instar) were used for propagation. These larvae were obtained from the laboratory insectary colony (continuous for more than 20 years) and were reared on standard artificial wheat germ diet (Wilkinson et al., J. Econ. Entomol. 65: 264–268 (1972)] until they reached the mid-4th instar. Five hundred larvae were visually selected for uniformity in size; each was placed on artificial diet (895 mm$^2$) in an individual cell of a compartmentalized disposable plastic tray (Ignoffo and Boening, supra), treated with 0.1 ml ($4.48 \times 10^4$ IB; 50 IB/mm$^2$) aqueous suspension of the HPV-85-CLMEV. The trays were incubated at 26° C. (constant darkness) for four days. Larvae were dead, flaccid, and beginning to liquefy after exposure for four days. At this time the trays were placed in a $-70°$ C. freezer (for 48 hr) to prevent further liquefaction of infected cadavers. The 430 frozen larvae (integument intact) of the original 500 larvae treated were selected from harvesting of the HPV-85-CLMEV IB.

EXAMPLE 2

Harvesting Protocol

An aqueous IB suspension was prepared by placing frozen larvae in SDW (1 larva/1.0 ml) in a "Sorvall" homogenizer for three min at 6,000 rpm. The resulting homogenate was filtered through nylon organdy, divided into 50-ml aliquots, placed in 50-ml centrifuge tubes, and spun at 2,000 rpm for 30 sec to sediment large tissue debris. IB were pelleted at 7,000 rpm for 10 min; the supernatant was discarded, and the pellets were resuspended in equal volumes of SDW. This process was repeated 3X. IB in the final washed suspension (225 ml) were counted (improved Neubauer, bright-line hemocytometer, phase contrast 500X). The concentration of IB in the OS was $1.72 \times 10^8$ IB/ml (SEM=0.23). Thirteen 1.0-ml aliquots were removed from the 225 ml OS, placed in 15-ml sterile disposable screw-top plastic tubes, and frozen at $-4°$ C. for use in future bioassays. These aliquots were subsequently thawed, diluted as required, and used in other tests. The procedure precluded thawing and re-freezing of OS each time a bioassay was conducted.

EXAMPLE 3

Propagation of AcMEV Stock Suspension

The alfalfa looper, *Autographa californica* (Speyer) multiple embedded nucleopolyhedrosis virus (AcMEV) was a lyophilized powder obtained from Dr. Fred Steward, USDA-ARS, Western Cotton Research Laboratory, Phoenix, Ariz. This material contained ca. $6.0 \times 10^9$ PIB/g and had been in frozen storage as a reference sample since 1974. The original propagate was prepared by suspending 100 mg of the powder in 100 ml of SDW in a volumentric flask. Serial dilutions and hemocytometer counts were made to prepare 50 ml of inoculum containing $8.89 \times 10^5$ IB/ml. Due to the lengthy storage time (12 yrs) and the use of 4th instar *T. ni* larvae as propagants, an arbitrary concentration of 100 IB/mm² of diet surface as selected. Standard diet (containing inhibitors) was also used to reduce the probability of bacterial contaminants. Nine diet trays (50 larvae each, in compartmentalized individual cells) were treated and incubated (total darkness) at 26° C. infected larvae demonstrated classic signs of NPV infection and began dying four days post-treatment. In an attempt to alleviate a recurring problem with secondary bacterial contamination, 320 lethargic and dead flaccid larvae were collected, placed in sterile disposable petri dishes (10 cm diameter), and incubated at 30° C. for an additional day until all larvae had liquefied. The resulting tissue homogenate was added to 90 ml SDW, filtered through nylon organdy, and found to be contaminated with a bacillus type bacteria (later traced to the artificial diet trays). The homogenate was substantially cleaned with differential centrifugation and the IB were pelleted at 7,000 rpm for 10 min. The pellet was then treated with 50 ml of a 3.3% (w/v) sodium deoxycholate solution (to lyse remaining bacterial cells) and incubated at 26° C. ca. 24 hours. The IB were pelleted (as before) from the sodium deoxycholate which was decanted, and the IB were resuspended in 50 ml of SDW and similarly washed 2X. After the final wash, the pelleted IB were resuspended in 70 ml SDW, which was designated at the AcMEV OS and was the source of all additional bioassays utilizing AcMEV. Hemocytometer counts determined each ml to contain $2.736 \times 10^9$ IB/ml OS. Twelve 1.0-ml aliquots of the AcMEV OS were removed, and each was placed in a separate 15-ml sterile plastic screw-top tube, labeled, and frozen for use in future bioassays.

EXAMPLE 4

Dose-Mortality, Time-Mortality, and Susceptibility Tests

Dose and time mortality studies were conducted with HPV-85-CLMEV and AcMEV on the following neonatal larvae: *Agrotis ipsilon, Heliothis subflexa, H. virescens, H. zea, Spodoptera frugiperda, Syngrapha falcifera,* and *Trichoplusia ni* (AcMEV not tested against *S. falcifera; S. falcifera* colony was lost before AcMEV was propagated).

EXAMPLE 5

HPV-85-CLMEV vs *Syngrapha falcifera* Neonates

Dose-mortality response was determined for neonate *S. falcifera* and *T. ni* larvae. Preliminary broad-dose screening tests indicated that the $LC_{50}$ would be $<1.0$ IB/mm². Aqueous suspensions containing $1.6 \times 10^7$ IB/ml were used to prepare serial dilutions, which were bioassayed using the contaminated diet surface method [Ignoffo and Boening, supra]. Neonatal larvae were bioassayed against IB concentrations of 0.75, 0.50, 0.25, 0.10, and 0.05 IB/mm² of diet surface. Fifty larvae were used per concentration, and each was replicated 4X over four consecutive days for a total of 200 larvae/concentration; appropriate controls (50 larvae untreated diet) were run concurrently. Larvae fed ad lib (one larva/cell) on the treated diet for 10 days (mortality was recorded daily), at which time the test was terminated. Trays were maintained in incubators (total darkness) at 26° C. Larval mortality for each concentration was calculated and corrected [Abbott, J. Econ. Entomol. 18: 265-267 (1925)] when needed. The 10-day mortablity data was transformed to percentages and subjected to probit analysis, and regression equations were calculated [Finney, Probit Analysis, 3d ed., Cambridge Univ. Press, London (1971); Busvine, A Critical Review of the Techniques for Testing Insecticides, Commonwealth Agric. Bureau, 345 pp. (1971)]. Confidence limits at the 95% probability level were calculated for the $LC_{50}$'s. Identical protocol was followed by the AcMEV vs *T. ni* neonates; *S. falcifera* neonates were not bioassayed against AcMEV. Time mortality curves (percent dead larvae/treatment) were developed for the aforementioned species by plotting the number of dead larvae for each treatment at 24-hr intervals (between 1600–1630 hours daily) for the 10day test period.

EXAMPLE 6

Susceptibility/Host Range Tests

During the course of these investigations, susceptibility and host range tests were limited to the lepidopterous species in culture at the USDA-ARS-BCIRL, Columbia, Mo.; larval stages of seasonally available field-collected lepidoptera in central Missouri; and certain colonies from faculty members of the University of Missouri Entomology Department, Columbia, Mo. Cooperators from USDA laboratories in Beltsville, Md.; Stoneville, Miss.; Fresno, Calif.; and Tifton, Ga., also conducted screening tests of the HPV-85-CLMEV against selected lepidopteran larvae maintained at these laboratories. A wide variety of hosts (and stages) were tested for susceptibility to the HPV-85-CLMEV. Standard stock concentrations (doses) of 10 and 100 IB/mm$^2$ of diet substrate (artificial or natural host plant) were selected (as representative of a realistic range) for challenging larvae in susceptibility bioassays. The 100 IB/mm$^2$ concentration equalled the recommended application rate of "ELCAR" (113.4 g, $4 \times 10^9$ IB/g AI). Larval susceptibility to these concentrations (i.e., classic signs/symptoms; microscopic confirmation) within the 10-day test period should closely approximate realistic field applications. Doses were increased proportionally for certain species due to their advanced stage (e.g., 3d-4th instar cutworms) and lower probability of eliciting infection within the 10-day exposure period.

EXAMPLE 7

Preparation of a Wettable Powder Formulation

A standardized, stabilized, wettable powder formulation was prepared as a reference/standard for future investigations [Cunningham, "Polyhedrosis Viruses Infecting the Eastern Hemlock Looper, *Lambdina fiscellaria*," in Proc. 4th Int. Colloq. Insect Pathol., College Park, MD (1971); Martignoni, "Production, Activity, and Safety of the Douglas-Fir Tussock Moth Nucleopolyhedrosis Virus," USDA, Forest Serv. Tech. Bull, No. 1585 (1978)]. The procedure was a modification of that described by Vail et al. [supra]. A homogenate was made of 500 5th instar *T. ni* larvae, which resulted in a 200-ml suspension containing $1.135 \times 10^9$ IB/ml. The suspension was centrifuged in a 250-ml "Nalgene" centrifuge bottle at 7,000 rpm for 10 min; the supernatant was discarded. The pellet was resuspended in 50 ml of 3.3% sodium deoxychloate (DOC) solution (for lysis of bacteria and cells) and incubated at 27° C. for ca. 20 hours. The suspension was then centrifuged as before to remove the DOC. The pellet was washed 2X by suspending in 150 ml of SDW and spinning at 7,000 rpm for 10 min. After the second wash, the pellet was resuspended in 150 ml of SDW and placed into a 1200 ml "Virtis" freeze-dry container along with 350 g of reagent grade D(+) #2248 lactose (monohydrate powder α-lactose) (J. T. Baker, Inc.) to form a thick slurry (lactose was used in lieu of maltose). The lyophilization flask was rolled to distribute the slurry evenly in the flask, placed in a −70° C. freezer for 1 hour, then lyophilized for 24 hours. The material was removed from the flask, pulverized with a mortar and pestle, and sieved through a No. 42 brass screen (345μ) onto waxed paper. This resulted in a very uniform white powder. The lyophilized preparation was stored in the freezer (−4° C.) overnight prior to quantification of IB/g and bioassay for activity.

EXAMPLE 8

Determination of IB/g

Ten grams of the powder was placed in a 100-ml volumetric flask and q.s.'d to 100 ml. The suspension was placed in a 200-ml beaker and sonified briefly (75-100 watts for 1 min) to disrupt any clumps. Serial dilutions were made and hemocytometer counts were conducted to determine the number of IB/g of lyophilized powder. The suspension was then adjusted to a concentration of 8950 IB/0.1 ml and bioassayed against 3d instar *T. ni, H. zea, H. virescens,* and *S. frugiperda* larvae to verify potency/infectivity.

EXAMPLE 9

Pathology and Microscopy

Infected larvae became lethargic, ceased feeding, and turned milky-white prior to death and rupture of the integument (liquefaction). IB were readily observable with phase contrast (500X) microscopy in aqueous mounts of excised infected tissue or in the blood cells and hemolymph.

EXAMPLE 10

Transmission Electron Microcopy

Inclusion bodies were pelletized from an aqueous suspension (OS) at 15,000 rpm for 10 min in an "Eppendorf" 5412 centrifuge. The IB were fixed in 1% glutaraldehyde (pH 7.2) at 4° C. for 2 hours, washed in 5% sucrose-sodium cacodylate buffer (pH 7.2) for 4 hours with four changes at 1-hr intervals, fixed in 2% osmium tetroxide (1 hr), washed in sucrose-sodium cacodylate buffer (10 min), and dehydrated in a series of 20, 40, 60, 80, 90, and 100% ethanol. IB remained in the 100% ethanol for 30 min; they were then centrifuged at 15,000 rpm for 10 min. The pellets were infiltrated and embedded in Spurs medium, sectioned (0.7-1.0 μm) with an LKB 2088 Ultratome V. Sections were stained with 1% ethanolic uranyl acetate (10 min) followed by a deionized water rinse and lead citrate stain (2 min). They were then rinsed in SDW, dried, and examined with a JEOL 100S electron microscope at 80 kV.

We claim:

1. A virus having the identifying characteristics of HPV-85-CLMEV, ATOC No. VR 2237.

2. A method of controlling insects comprising applying to an insect or an insect habitat an insecticidally effective amount of a virus having the identifying characteristics of HPV-85-CLMEV, ATCC No. VR 2237.

3. A method of controlling insects as described in claim 2 wherein said insects are lepidoptera.

4. An insecticidal composition comprising an insecticidal amount of a virus having the identifying characteristics of HPV-85-CLMEV, ATCC No. VR 2237, and an inert carrier.

5. An insecticidal composition as described in claim 4 wherein said inert carrier is lactose.

* * * * *

UNITED STATES PATENT AND TRADEMARK OFFICE
CERTIFICATE OF CORRECTION

PATENT NO. : 4,911,913

DATED : March 27, 1990

INVENTOR(S) : Donald L. Hostetter and Benjamin Puttler

It is certified that error appears in the above—identified patent and that said Letters Patent is hereby corrected as shown below:

Column 2, line 28, delete "Copper" and insert -- Cooper -- ;
Column 2, line 54, delete "TB" and insert -- IB -- ;
Column 2, line 55, delete "EIB" and insert -- IB -- .
Column 3, line 32, delete "Prepagation" and insert -- Propagation -- ;
Column 3, line 38, delete "bacterial" and insert -- bacteria -- .
Column 5, line 54, delete "*Piersis*" and insert -- *Pieris* -- .
Column 9, line 33, delete "Steward" and insert -- Stewart -- .

Signed and Sealed this

Twentieth Day of August, 1991

Attest:

HARRY F. MANBECK, JR.

Attesting Officer     Commissioner of Patents and Trademarks